United States Patent
Kärcher et al.

(10) Patent No.: US 12,064,132 B2
(45) Date of Patent: Aug. 20, 2024

(54) SHAFT FOR AN ENDOSCOPIC INSTRUMENT, ENDOSCOPIC INSTRUMENT AND ENDOSCOPIC SYSTEM

(71) Applicant: KARL STORZ SE & Co. KG, Tuttlingen (DE)

(72) Inventors: Daniel Kärcher, Tuttlingen (DE); Jochen Stefan, Tuttlingen (DE); Tobias Unger, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 701 days.

(21) Appl. No.: 16/816,598

(22) Filed: Mar. 12, 2020

(65) Prior Publication Data
US 2020/0297370 A1 Sep. 24, 2020

(30) Foreign Application Priority Data
Mar. 20, 2019 (DE) ..................... 10 2019 107 091.0

(51) Int. Cl.
A61B 17/29 (2006.01)
A61B 17/3201 (2006.01)
A61B 17/00 (2006.01)

(52) U.S. Cl.
CPC ...... *A61B 17/2909* (2013.01); *A61B 17/3201* (2013.01); *A61B 2017/00477* (2013.01); *A61B 2017/2901* (2013.01); *A61B 2017/2931* (2013.01)

(58) Field of Classification Search
CPC .. A61B 2017/00477; A61B 2017/2901; A61B 2017/2931; A61B 2017/00464
See application file for complete search history.

(56) References Cited

U.S. PATENT DOCUMENTS 4,985,035 A * 1/1991 Torre ................. A61B 17/3213
606/167
5,413,573 A * 5/1995 Koivukangas ......... A61B 90/50
606/1
(Continued)

FOREIGN PATENT DOCUMENTS

WO 2012/061646 A1 5/2012

OTHER PUBLICATIONS

Search Report, DE 10 2019 107 091.0, dated Feb. 3, 2020 (in German) (10 pp.).

*Primary Examiner* — Alexander J Orkin
(74) *Attorney, Agent, or Firm* — Eversheds Sutherland (US) LLP (57) ABSTRACT

A shaft according to the application for an endoscopic instrument has a connecting section arranged in a distal end region of the shaft, with a connecting device for connection, in particular in the manner of a bayonet connection, with a replaceable working insert being formed at said connecting section, the connecting device having a first engagement structure for a connection engagement of an engagement element of a working insert of a first type, and the connecting device having a second engagement structure for a connection engagement of an engagement element of a working insert of a second type, wherein the first and the second engagement structures are arranged and/or formed differently. The application also relates to an endoscopic instrument and an endoscopic system.

1 Claim, 6 Drawing Sheets

(56) References Cited

U.S. PATENT DOCUMENTS

| | | | |
|---|---|---|---|
| 5,499,985 A * | 3/1996 | Hein | A61B 17/162 |
| | | | 606/1 |
| 5,527,339 A | 6/1996 | Koscher et al. | |
| 5,741,084 A * | 4/1998 | Del Rio | A61B 17/1633 |
| | | | 285/376 |
| 5,782,853 A * | 7/1998 | Zeevi | A61B 17/3468 |
| | | | 606/187 |
| 5,888,200 A * | 3/1999 | Walen | B25F 3/00 |
| | | | 606/167 |
| 5,954,259 A | 9/1999 | Viola et al. | |
| 6,059,719 A * | 5/2000 | Yamamoto | A61B 17/00234 |
| | | | 606/1 |
| 6,468,279 B1 * | 10/2002 | Reo | A61B 17/16 |
| | | | 606/104 |
| 2003/0165794 A1 * | 9/2003 | Matoba | A61C 1/0007 |
| | | | 433/114 |
| 2005/0165443 A1 * | 7/2005 | Livneh | A61B 17/29 |
| | | | 606/205 |
| 2008/0021278 A1 | 1/2008 | Leonard et al. | |
| 2008/0294192 A1 * | 11/2008 | Stefan | A61B 17/1608 |
| | | | 606/205 |
| 2012/0023733 A1 * | 2/2012 | Cannell | B23B 31/103 |
| | | | 403/375 |
| 2015/0174754 A1 * | 6/2015 | Petit | B25G 1/08 |
| | | | 81/489 |
| 2019/0125476 A1 * | 5/2019 | Shelton, IV | A61B 17/1285 |
| 2020/0015829 A1 * | 1/2020 | Khalili | A61B 17/320758 |

* cited by examiner

SHAFT FOR AN ENDOSCOPIC INSTRUMENT, ENDOSCOPIC INSTRUMENT AND ENDOSCOPIC SYSTEM

TECHNICAL FIELD

The present invention relates to a shaft for an endoscopic instrument, in particular for an endoscopic medical instrument. The present invention also relates to an endoscopic instrument with such a shaft and to an endoscopic system.

BACKGROUND OF THE INVENTION

Endoscopic surgical techniques have prevailed for a variety of surgical procedures. In this case, an endoscopic instrument set, which in particular can comprise an endoscope and one or more endoscopic instruments, is routed through a natural or an artificial body opening created with the aid of an incision to an operation area located inside the body. For this purpose, endoscopic instruments have a long extended shaft, at the distal end of which, i.e., the end away from the user, a tool is arranged to perform surgical manipulations, which tool can be actuated by a handlebar arranged at the proximal end, i.e., the end close to the user, of the shaft via an elongated transmission element arranged in the shaft. The shaft can be rigid or flexible. During an endoscopic procedure, the handlebar remains outside the body opening, while the shaft with the tool is inserted through the body opening.

According to a widespread type, endoscopic instruments have a working insert which carries the tool at its distal end and which may also comprise the transmission element. Here, the working insert is detachably connected to the shaft of the instrument. In particular, after having performed an endoscopic procedure, the instrument can be disassembled for cleaning and/or sterilization, the working insert being detached from the shaft and removed from a shaft tube of the shaft; the handlebar can also be separated from the shaft. Furthermore, different tools may be required depending on the type and progress of an endoscopic procedure. Therefore, a working insert required in each case is usually selected and inserted into the shaft and connected to it. Likewise, a working insert with a first type of tool, such as a cutting tool, can be replaced by another working insert with a different type of tool, such as a gripping tool. For the detachable connection of the working insert to the distal end region of the shaft, a connection which is designed in the manner of a bayonet connection is particularly advantageous.

DE 100 38 576 C1 discloses a medical instrument with a shaft and a tool removably fastened to a distal end of the shaft, the shaft having an inner shaft and a tubular shaft surrounding the inner shaft and being longitudinally displaceable relative thereto. The tool is locked to the shaft in a locking position of the tubular shaft advanced relative to the inner shaft and can be removed from the shaft in a release position of the tubular shaft retracted relative to the inner shaft. A distal end of the inner shaft has a bayonet-like recess with a section which initially runs axially and then circumferentially, a holder being formed at the proximal end of the tool, which holder can be inserted into the bayonet-like recess with a transversely running section.

According to DE 10 2012 007 648 A1, a medical instrument comprises an outer shaft, a handling device at the proximal end of the outer shaft, a tool at the distal end of the outer shaft, with a first effecting device for a first function and a second effecting device for a second function, and a first and a second transmission device in the outer shaft for transmitting a force or a torque for controlling the first or second effecting devices. The tool and the outer shaft have coupling devices for a detachable mechanical connection of the tool to the distal end of the outer shaft. The coupling devices can comprise bayonet coupling devices.

Generic shafts for medical endoscopic instruments are sold by KARL STORZ SE & Co. KG, for example under the name "ClickLine® Metall-Außenschaft" with the article number 33300 and under the name "RoBi® Metall-Außenschaft" with the article number 38600.

The detachable connection between the shaft and the working insert can in principle result in an undesirable play, in particular due to the tolerance fields provided at the connection point between the shaft and the working insert. This can impair the actuation of the working insert, for example a so-called "lost motion" can lead to inaccurate actuation of the tool. When implementing narrower tolerance fields, on the other hand, there are restrictions with regard to compatibility with existing instruments, for example the use of a working insert corresponding to a wider tolerance field with a shaft that is designed for narrower tolerances may be excluded.

SUMMARY OF THE INVENTION

It is an object of the present invention to provide a shaft for an endoscopic instrument, an endoscopic instrument and an endoscopic system, the disadvantages mentioned above being avoided as far as possible. In particular, it is an object of the invention to provide a shaft for an endoscopic instrument as well as an endoscopic instrument and an endoscopic system, wherein a higher actuation accuracy can be achieved and at the same time a high degree of insert flexibility and compatibility is guaranteed.

This object is achieved by a shaft according to claim 1, by an endoscopic instrument according to claim 14 as well as by an endoscopic system according to claim 15.

Advantageous developments of the invention result from the dependent claims.

A shaft according to the invention is designed for an endoscopic instrument, in particular for a medical endoscopic instrument, and can therefore be used for minimally invasive surgical procedures. Such a shaft can be designed as part or assembly of an endoscopic instrument, in particular a medical endoscopic instrument, or can be assembled together with other components to form an endoscopic instrument. The shaft is in particular rigid or essentially rigid and can be part or assembly of a rigid endoscopic instrument. On the other hand, the shaft can also be designed to be flexible.

A shaft according to the invention has a connecting section which is arranged in a distal end region of the shaft. The connecting section can be formed, for example, by a distal end section of the shaft or a shaft tube which is encompassed by or represents the shaft. A connecting device is formed at the connecting section for a detachable connection between the shaft and a working insert, whereby the working insert is replaceably connected with the shaft, that is, one working insert can be replaced by another. Such a working insert can in particular have a surgical tool, which can comprise, for example, one or more pivotably mounted jaws, which can be actuated by a longitudinal displacement of a transmission element connected to the jaws and routed inside the shaft with a handlebar arranged at the proximal end of the shaft. For this purpose, the working insert can be inserted into the shaft at least in sections and connected to the connecting section of the shaft. In this way, the connecting section can, for example, enclose or surround a section of the working insert, so that a particularly reliable connection between the shaft and a working insert can be implemented, the shaft serving to support the working insert.

The connection is configured in particular in the manner of a bayonet connection. Accordingly, in particular a connection in the manner of a bayonet lock can be produced between the connecting device and a working insert. Such a bayonet connection can be produced in a simple manner, in particular with little handling effort, and at the same time ensures a high degree of connection reliability. To create a connection in the manner of a bayonet lock, it can be provided that the two connection partners can be inserted into one another along their longitudinal axes and can be secured or fixed by turning them in opposite directions. In particular, a working insert can be inserted into the shaft and then rotated relative to the shaft, that is to say rotated about a longitudinal axis of the shaft. This can be carried out with only a few simple steps.

The connecting device has a plurality of engagement structures for the connection engagement of working inserts of different structural shapes, which are referred to here as different types of working inserts. For this purpose, the connecting device comprises at least one first engagement structure for a connection engagement of an engagement element of a working insert of a first type, i.e., of a first type of working insert. The engagement structure associated with the connecting device can be referred to in particular as a bayonet engagement structure and the engagement element associated with the working insert can in particular be referred to as a bayonet engagement element or bayonet blade. Through a bayonet-like engagement of the engagement element of the working insert of the first type in the first engagement structure of the connecting device, in particular a bayonet connection can be produced, by means of which a base of the working insert is fixedly connected in the longitudinal direction of the shaft to its distal end section, wherein the connection can also be released again by an opposite rotation about a longitudinal axis of the shaft.

According to the invention, the connecting device further comprises at least one second engagement structure for a connection engagement of an engagement element of a working insert of a second type, i.e., of a second type of working insert. By engaging the engagement element of the second type of working insert in the second engagement structure of the connecting device, a connection, in particular a bayonet connection, can be created in a corresponding manner, by means of which a base of the working insert of the second type is fixedly connected in the longitudinal direction of the shaft to its distal end section, wherein the connection can also be released by an opposite rotation about the longitudinal axis of the shaft.

According to the invention, the first and the second engagement structures are arranged and/or designed differently. This means that the first and the second engagement structures are arranged, for example, in different positions, in particular separately from one another, on the connecting section and/or are dimensioned differently and/or have different shapes.

By the fact that the connecting device has a plurality of different engagement structures, wherein one type of working insert can be brought into connection engagement with one of the engagement structures and whereby a connection engagement with another engagement structure can be produced by replacing the type of working insert with another type of working insert, it is possible to connect working inserts of different types in an optimal way to the connecting section and thus to the shaft. In particular, the different engagement structures can be designed for different connection tasks or connection properties.

The configuration according to the invention provides the possibility, for example, of designing at least one of the engagement structures for already existing types of working inserts and a further engagement structure for a new type of working insert. The different engagement structures can also be designed with regard to different tolerance fields of the different types of working inserts. The shaft can also be used together with already existing types of working insert due to the plurality of engagement structures. This ensures a high degree of replaceability and versatility in the use of the shaft.

According to an advantageous embodiment of the invention, the first and second engagement structures are arranged and/or designed differently in such a way that the first engagement structure permits the connection engagement with the engagement element of the working insert of the first type and blocks a connection engagement with the engagement element of the working insert of the second type, and that the second engagement structure permits the connection engagement only with the engagement element of the working insert of the second type and blocks a connection engagement with the engagement element of the working insert of the first type. This allows, in particular, a connection engagement only between the first type of working insert and the first engagement structure and, by replacing the type of working insert, a connection engagement only between the second type of working insert and the second engagement structure, while connection engagements between the engagement element of the first type of working insert with the second engagement structure and vice versa are impossible. Such a configuration of the connecting device can also be viewed as a mechanical coding. Such a mechanical coding can advantageously be designed by differently shaped, dimensioned and/or arranged engagement structures. To produce a mechanical coding, accordingly, the engagement structures can have different shapes, in particular each have their own or individual shape. Likewise, the engagement structures can each be dimensioned differently, so that a coding is formed due to the different sizes of the engagement structure. Finally, it is also possible to form a coding by means of a specific arrangement of the engagement structures, in particular by arranging the different engagement structures at different sections or positions of the shaft.

Such coding can further improve operational reliability as well as user-friendliness. Such a coding can in particular facilitate the establishment of a correct connection between the shaft and a working insert and reduce the risk of incorrect or inadequate connections between the shaft and working insert. The coding can be designed, for example, to allow only matched connection pairs and/or to block undesired connection pairs.

The first and the second engagement structures can advantageously be arranged differently in that the second engagement structure is arranged at a different distance from a distal end of the shaft in comparison with the first engagement structure. According to this embodiment, the connecting device thus has a second engagement structure for a connection engagement of an engagement element of a working insert of the second type, the second engagement structure being arranged at a distance from a distal end of the shaft, which differs from a corresponding distance of the first engagement structure, that is to say is smaller or larger, in particular by more than the manufacturing tolerances that may exist in the respective types of working inserts. In this way, a connection engagement between an engagement element of a working insert, which is arranged at a corresponding distance, for example, from a stop attachable to the distal end, with an engagement structure associated with the respective type of working insert, can be ensured in a simple and reliable manner, and at the same time an engagement with another type of the working insert, wherein the engagement element is disposed at a different distance therefrom, can be prevented.

According to a preferred embodiment of the invention, the connecting device has at least one recess running in the longitudinal direction, in particular at least one longitudinal slot or at least one longitudinal groove, the longitudinal slot or the longitudinal groove being designed for the longitudinal routing of an engagement element of a working insert according to the first and/or the second type. The longitudinal slot or the longitudinal groove can run in the longitudinal direction of the shaft, in particular approximately parallel to a longitudinal axis of the connecting section, and is preferably open in the distal direction in order to facilitate insertion of the engagement element when connecting the working insert to the shaft. A radial projection, which forms an engagement element of a working insert, can be routed through the longitudinal slot or the longitudinal groove, for example. In a particularly preferred manner, the longitudinal slot or the longitudinal groove is suitable for the longitudinal routing of the engagement element of both the first and the second type of working insert. The longitudinal slot or the longitudinal groove can be formed, for example, in a distal end section of a shaft tube, which distal end section represents the connecting section of the shaft, wherein the longitudinal groove is preferably formed inside the shaft tube.

The first and the second engagement structures are preferably formed in each case by a recess running in the transverse direction, in particular by a transverse slot running transverse to the longitudinal axis of the shaft or of the connecting section, or by a transverse groove running transverse to the longitudinal axis. Here, the transverse slot or the transverse groove of the first engagement structure is designed for longitudinal fixing of the engaging element of the working insert according to the first type and the transverse slot and the transverse groove of the second engagement structure for longitudinal fixing of the engaging element of the working insert of the second type. The transverse slots or transverse grooves are formed, for example, in a distal end section of a shaft tube which forms the connecting section of the shaft, the transverse groove preferably being formed inside the shaft tube.

The engagement structures designed as transverse slots or transverse grooves are further preferably formed separately from one another. In a particularly preferred manner, the engagement structures or the transverse slots or transverse grooves can each run transversely to the longitudinal slot or to the longitudinal groove and open into the longitudinal slot or the longitudinal groove. Such an arrangement, in particular of longitudinal slots and transverse slots, can be easily implemented in terms of production technology. In addition, this can in particular ensure the possibility of establishing a connection in the manner of a bayonet lock with a working insert, as well as by a corresponding arrangement of the longitudinal groove and transverse grooves or also of the longitudinal slot and transverse grooves as well as of the longitudinal groove and transverse slots. In this case, a projection or a correspondingly shaped form element of a working insert can be introduced in the longitudinal direction of the shaft through a longitudinal slot or a longitudinal groove and, starting from the longitudinal slot or the longitudinal groove, can be transferred into one of the transverse slots or transverse grooves. The transverse slots or transverse grooves serve for the longitudinal fixation of a projection or of an engagement element of a working insert designed corresponding to the respective transverse slot or the respective transverse groove. In this case, such a projection or such a form element of a working insert can project in radial direction relative to adjacent sections of the working insert.

It can furthermore be advantageous if the engagement structures, in particular the engagement structures designed as transverse slots or transverse grooves, are formed independently of one another and/or spaced apart from one another in a longitudinal direction of the connecting section. In a particularly preferred manner, the transverse slots, in particular the at least two transverse slots associated with a longitudinal slot or the at least two transverse grooves associated with a longitudinal groove, can be at different distances from the distal end of the shaft. In this way, a connection, in particular a bayonet-shaped connection and at the same time a mechanical coding can be made possible in a particularly simple and reliable manner. For example, a transverse slot or a transverse groove, which is arranged further away from the distal end of the shaft, can be designed for establishing a connection with a new type of working insert, wherein the greater distance from the distal end can ensure that this transverse slot or this transverse groove from previous types of the working insert, in which the corresponding engagement element is arranged at a shorter distance from the distal end, is not reached for a connection engagement. A suitable association of transverse slots or transverse grooves with certain types of working inserts can thus be established.

The first and second engagement structures are preferably designed differently in that the second engagement structure is dimensioned differently from the first. According to this embodiment, the connecting device thus has a second engagement structure for a connection engagement of an engagement element of a working insert of a second type, the second engagement structure having a dimensioning that differs from a corresponding dimensioning of the first engagement structure. For example, the second engagement structure corresponding to an engagement element of the second type of working insert can be designed to be larger or wider or deeper in the axial and/or radial direction than the first engagement structure associated with the first type of working insert, in particular by more than any existing manufacturing tolerances of the respective type of working insert. This allows in a simple and reliable way to ensure a connection engagement between a suitably configured engagement element of a working insert with an engagement structure dimensioned for the particular type of working insert and at the same time, prevents an engagement with a type of working insert the engaging element of which is dimensioned differently.

The first and second engagement structures are preferably dimensioned differently from one another in that they have different widths, the width in particular being a dimensioning in the longitudinal direction of the connecting section. In particular, the first and second engagement structures can be designed as transverse slots or transverse grooves, the transverse slot or the transverse groove of the first engagement structure having a width different from a width of the transverse slot or the transverse groove of the second engagement structure. For example, two transverse slots which are associated with a longitudinal slot or originate from the same longitudinal slot can have a different width. The same applies to two transverse grooves. The different widths of the transverse slots or transverse grooves can be formed corresponding to engagement elements designed as projections or form elements on different types of working insert. A transverse slot or a transverse groove with a relatively small width can thus block the connection engagement of an excessively wide projection or form element of another type of working insert. For example, it can be provided that a projection or form element of a first type of working insert is routed through the longitudinal slot to different transverse slots or transverse grooves, but can only be moved into a specific transverse slot or a specific transverse groove. In this way, it can be achieved in a particularly simple and reliable manner that a connection engagement between a correspondingly configured engagement element of a working insert of the first type is only possible with the first engagement structure and between a correspondingly configured engagement element of the second type of working insert is only possible with the second engagement structure.

If the engagement structures are designed as transverse grooves, the transverse grooves of the first and second engagement structures can alternatively or in addition to the different width have a different depth. Furthermore, alternatively or additionally, the transverse slots or transverse grooves can have different cross-sectional shapes. Also in this case, a corresponding coding can be implemented in a simple and reliable way.

According to a particularly preferred embodiment of the invention, the transverse slots or transverse grooves are arranged and designed differently in such a way that a transverse slot or a transverse groove at a greater distance from a distal end of the connecting section has a greater width than a transverse slot or a transverse groove at a smaller distance from the distal end. The connecting section can be designed, for example, as a distal end section of a shaft tube, which at the same time forms the distal end section of the shaft, so that in this case the transverse slot or the transverse groove with the greater width is at a greater distance from the distal end of the shaft than the transverse slot or the transverse groove with a smaller width. In this way, a second type of working insert with a larger dimensioned projection or form element can be routed through the longitudinal slot or the longitudinal groove, wherein, due to the larger dimensioning, an insertion into the transverse slot or the transverse groove of the first engagement structure, which has a smaller width, is blocked. Only a transverse slot or a corresponding transverse groove arranged further away from the distal end of the connecting section or of the shaft has a width suitable for the connection engagement with the projection or form element of the second type of working insert. In contrast, the transverse slot or the transverse groove of smaller width can be provided for a first type of working insert the corresponding projection or corresponding form element of which can be routed along the longitudinal slot or the longitudinal groove only up to the transverse slot and the transverse slot of smaller width, for example, due to a corresponding arrangement of the projection or form element, in particular due to corresponding length dimensions of the working insert of the first type. Such an arrangement and dimensioning of transverse slots can suitably achieve an association of transverse slots or transverse grooves with different types of working inserts. In this manner, with a single shaft, different connecting tasks can be implemented in a particularly advantageous manner.

Alternatively or in addition to an arrangement of the engagement structures, these being arranged one behind the other in the longitudinal direction of the shaft or at different distances from the distal end of the shaft, the different engagement structures can also be arranged at different radial distances relative to a longitudinal axis of the shaft. In this case, the shaft, in particular in the region of the connecting section, can be formed from two shaft sections arranged one inside the other. For example, a first longitudinal slot with a first transverse slot extending therefrom can be provided at a first radial distance from the longitudinal axis of the shaft, and a second longitudinal slot with a second transverse slot extending therefrom can be provided at a second radial distance from the longitudinal axis of the shaft, which is, for example, greater than the first radial distance; alternatively, longitudinal grooves and related transverse grooves can be provided at different radial distances from the longitudinal axis in a corresponding manner. In this way too, mechanical coding can be implemented in a simple and reliable manner.

According to a preferred configuration, the different engagement structures, in particular the engagement structures designed as transverse slots or transverse grooves, can be designed to generate different tolerance fields in connection engagement with different types of working insert. For example, a transverse slot or a transverse groove at a smaller distance from the distal end of the shaft can be designed for connection engagement with an already existing type of working insert and can accordingly be designed for a relatively wide tolerance field. In contrast, a transverse slot or a transverse groove at a greater distance from the distal end of the shaft can be designed for connection engagement with a new type of working insert, in which a narrower tolerance field can be implemented. To this end, in the new type of working insert, a narrower tolerance of pairs of parts can be used, based on the distance between the distal end of the connecting section and a distal side of a transverse slot, compared with a corresponding distance between a distal side of a projection which engages in the transverse slot when the connector is engaged, and a corresponding stop of the work insert. At least one of the engagement structures can thus be designed with respect to a relatively narrow tolerance field, in order to reduce the play between the shaft and the working insert when a corresponding connection is made with a suitable type of working insert. The accuracy of the actuation can thus be improved, since in this way a possible lost motion can be reduced or completely avoided. For example, when using new types of working insert, less play between the working insert and the shaft can be achieved. In addition, it can be avoided by such a configuration that the respective types of working insert come into connection engagement with an unsuitable engagement structure.

The connecting device preferably has multiple first engagement structures and multiple second engagement structures, the multiple first engagement structures being arranged offset with respect to one another in the circumferential direction of the connecting section and the multiple second engagement structures likewise being arranged offset with respect to one another in the circumferential direction. In particular, the connecting device can have two first engagement structures and two second engagement structures, which are arranged opposite each other in the circumferential direction of the connecting section. For example, the connecting device can have two or more longitudinal slots or longitudinal grooves, as a result of which a further improved routing when inserting a working insert to be connected is ensured and an improved connection can be made possible. Two longitudinal slots are preferably arranged opposite one another in the circumferential direction of the connecting section, i.e., the longitudinal slots are offset from one another by 180° with respect to the longitudinal axis of the connecting section and are therefore arranged symmetrically. When connected to a working insert, uniform force transmission can be ensured in this way. It is further preferred that at least two transverse slots can be provided for each longitudinal slot. Preferably, all transverse slots starting from the respective longitudinal slot can run in the same orientation in the circumferential direction, such as clockwise from the respective longitudinal slot, as viewed from the distal end of the shaft. In a particularly preferred manner, the combination of a longitudinal slot and at least two transverse slots can be provided several times in an identical manner. Two or more such combinations can be arranged or formed symmetrically relative to a longitudinal axis of the shaft. Furthermore, the above statements apply in the same way to any combination of a longitudinal slot and at least two transverse slots, it also being possible for grooves to be provided instead of slots.

It can furthermore be advantageous if the connecting section is designed as part of an outer shaft, in particular as a distal end section of a shaft tube which forms the outer shaft. The shaft tube, at least the connecting section, is preferably rigid. Such an outer shaft can preferably be provided with a sheath, for example, by which a protective function or electrical insulation is provided. For example, the shaft tube can be made of a metallic material, such as stainless steel, and the sheath can be made of a plastic material, which can rest on the outside of the shaft tube in the form of a shrinking tube. The outer shaft can also be designed to route a transmission element inside, for example a drawbar or an inner shaft. A tool of a working insert connected to the shaft can be actuated in an advantageous manner by means of such a transmission element. The outer shaft can surround the transmission element in a suitable manner and route it movably. The shaft according to the invention may in particular be totally designed as an outer shaft or have an outer shaft, wherein the connecting section is advantageously formed at a distal end of the outer shaft.

Another aspect of the present invention relates to an endoscopic instrument, in particular a medical endoscopic instrument, with a shaft which is formed as previously described, and with at least one working insert which is detachably connected to the connecting section of the shaft via the connecting device of the shaft. If the connection between the working insert and the shaft is now detached, another working insert, for example a different type of working insert, can be connected to the shaft instead of the removed working insert. Depending on the type of working insert, a connection engagement with different engagement structures of the shaft can be established. The engagement structures can therefore be designed or structured for different connection tasks.

The working insert has, in particular, a surgical tool which can be formed by one or more pivotably mounted jaw parts which are connected to an elongate transmission element and can be actuated by a longitudinal displacement of the transmission element from the proximal end of the shaft. Preferably, the working insert comprises a base which is, as described above, designed for connecting to the connecting section particularly in the manner of a bayonet connection, and which carries at least one engagement element for this purpose. The base is designed in particular approximately cylindrical in sections and dimensioned for insertion into the connecting section of the shaft, the insertion depth being limited by a stop. The at least one engagement element is arranged at such a distance from the stop that it can be brought into connection engagement in an engagement structure of the connecting section. At a distal end of the base, for example, a fork device is arranged for the pivotable mounting of at least one jaw part of the surgical tool, which can be designed, for example, for cutting or grasping tissue. The fork device can have two opposite pivot bearings. Furthermore, the base can have a feed-through for the transmission element connected to the pivotable jaw parts and can accordingly be tubular. The transmission element can thus be passed through the shaft and extend as far as the fork device. At the proximal end of the shaft, a handle, for example a handlebar, can be detachably attached, which can be connected to the transmission element in order to transmit an actuation by a user to the transmission element and further to the tool of the working insert.

Another aspect of the present invention relates to an endoscopic system, in particular a medical endoscopic system, with a shaft designed as described above and with at least one working insert of the first type and at least one working insert of the second type. Here, as described above, the working insert of the first type is designed for connection engagement with the first engagement structure of the connecting section of the shaft and the working insert of the second type is designed for connection engagement with the second engagement structure of the connecting section. The working insert of the first and that of the second type are preferably designed differently in such a way that the working insert of the first type only enables connection engagement with the first engagement structure and that of the second type only enables connection engagement with the second engagement structure. In particular, the working insert of the second type has at least one engagement element which is arranged and/or dimensioned and/or shaped differently in comparison to at least one engagement element of the work element of the first type and thereby only permits the connecting section with the respectively associated engagement structure. The endoscopic system thus comprises the shaft and a plurality of different types of working insert, which can be connected individually and interchangeably to the connecting section of the shaft by the connecting device. The endoscopic system is therefore formed by combining the shaft with at least one working element of the first type of working insert and at least one working element of the second type of working insert, wherein, as described above in relation to the shaft, a connection engagement with the different engagement structures of the shaft is established depending on the type of working insert.

Because a first type of working insert can be brought into connection engagement with the first engagement structure and a connection engagement with the second engagement structure can be established by replacement with a second type of working insert, the engagement structures can be designed for different connection tasks and accordingly, the working inserts can be configured differently. On the one hand, this increases operational reliability and at the same time guarantees a wide range of possible uses.

According to a particularly preferred configuration of the endoscopic system, a tolerance field between the first type of working insert and the corresponding first engagement structure can differ from a tolerance field between the second type of working insert and the corresponding second engagement structure. In particular, the respective tolerances of pairs of parts can differ. For example, conventional tolerance fields can be implemented for existing types of working inserts, so that backward compatibility with such types of working insert is maintained, and at the same time, a narrower tolerance field can be selected and implemented for new types of working insert, so that a lower degree of play is achieved when using such types of working insert, or any lost motion can be reduced or avoided altogether.

According to a method according to the invention for configuring an endoscopic instrument, an endoscopic instrument is provided that comprises a shaft, which is designed as described above, and a working insert according to the first type, which is connected to the shaft. The at least one engagement element of the working insert is thus in connection engagement with the at least one first engagement structure of the connecting section of the shaft. By rotating about the longitudinal axis of the shaft or the connecting section and removing it in the distal direction, the working insert is detached from the connecting device and separated from the shaft, in particular in the manner of a bayonet connection. A working insert according to the second type is also provided. By inserting it into the shaft from the axial direction and finally rotating it about the longitudinal axis, said working insert according to the second type is connected to the shaft. The working insert of the second type is configured differently from the first one such that the at least one engagement element of the second type of working insert comes into connection engagement with the second engagement structure of the connecting section of the shaft.

Accordingly, the at least one engagement element of the second type of working insert is arranged and/or configured differently than that of the first type of working insert. The working inserts can be replaced, for example, during an endoscopic procedure, or after an endoscopic procedure the working insert of the first type can be detached from the shaft, at least the shaft can be cleaned and/or sterilized, and the working insert of the second type can be connected to the shaft before another endoscopic procedure. The method according to the invention can comprise further steps, for example the removal and/or attachment of a handlebar.

The above statements regarding the shaft also apply in the same way to the endoscopic instrument and to the endoscopic system and to the method for configuring the endoscopic instrument.

It is to be understood that the features mentioned above and those yet to be explained below can be used not only in the combination indicated in each case, but also in other combinations or on their own without departing from the scope of the present invention.

BRIEF DESCRIPTION OF THE DRAWINGS

Further aspects of the invention result from the following description of a preferred exemplary embodiment and the attached drawing. The Figures each show schematically.

DETAILED DESCRIPTION

Figure 1:
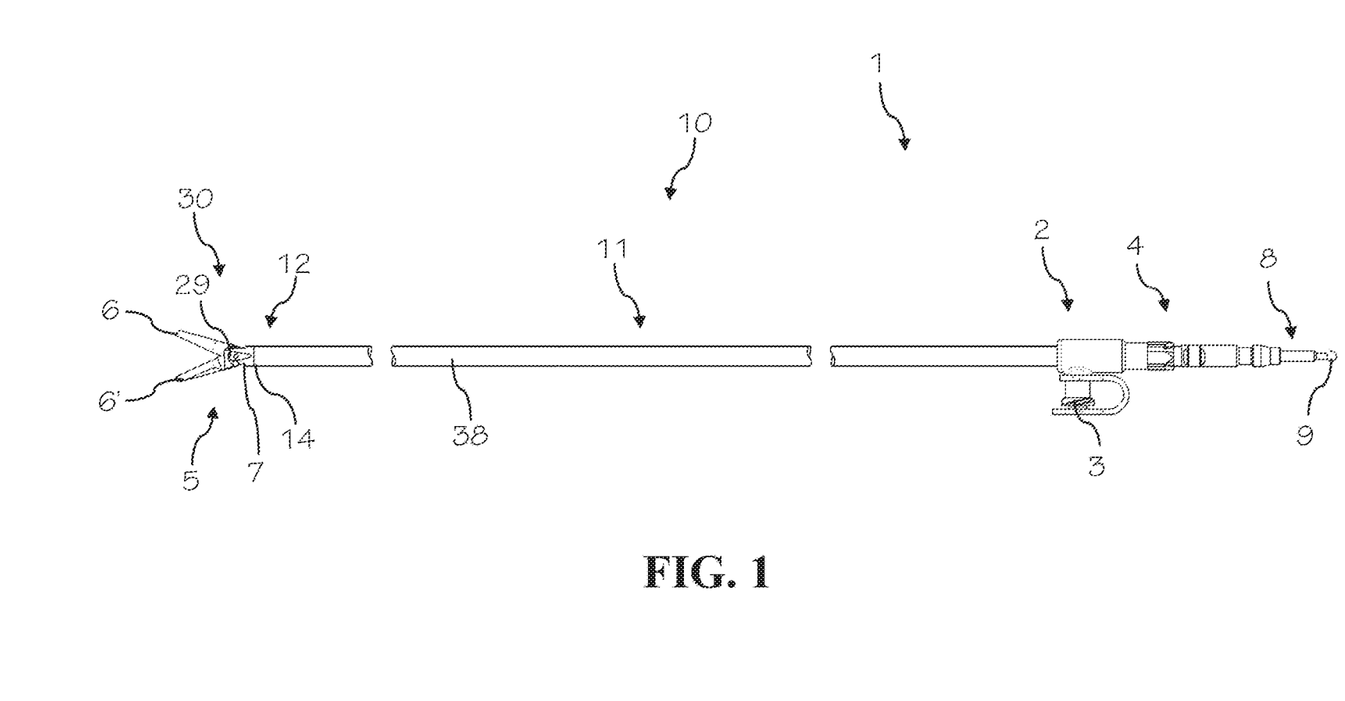
FIG. 1 shows a shaft according to an embodiment of the present invention with a working insert inserted in a side view.

As illustrated in FIG. 1, a shaft 10 for a medical endoscopic instrument 1 according to an exemplary embodiment of the present invention comprises a proximal section 2, an elongated central section 11 and a distal end section 12. Shaft 10 is dimensioned for insertion into a cavity inside the body, for example, for insertion into a working channel of an endoscope, which is inserted into the cavity inside the body during an endoscopic procedure. Proximal section 2 of shaft 10 can have a connection 3, for example a rinsing connection, and a connecting mechanism 4, which is only illustrated by way of example in FIG. 1, for connection to a handlebar, not shown. Connecting mechanism 4 can be designed such that the handlebar can be rotatably attached, so that shaft 10 can be rotated relative to the handlebar about the longitudinal axis of shaft 10.

A tool 5 is connected to distal end section 12 of shaft 10 and, in the exemplary embodiment shown, is designed as a pair of scissors with two scissor blades 6, 6' that can be pivoted relative to distal end section 12 of shaft 10. Tool 5 is part of a working insert 30 which is inserted into shaft 10 on the distal side. Working insert 30 further comprises a base 7, which is designed on the distal side as a fork 29, in which scissor blades 6, 6' are pivotally mounted. Working insert 30 abuts on distal end 14 of shaft 10 with a stop of base 7. As will be explained in more detail below with reference to FIGS. 2 to 6, an insertion section 32 of base 7 is inserted and connected to in distal end section 12 of shaft 10, which distal end section 12 is designed as a connecting section 16 for this purpose (see FIGS. 2 to 6).

Inside shaft 10 is a drawbar 8 that is slidably disposed in the longitudinal direction of shaft 10. The proximal end of drawbar 8 is formed by a connecting element, for example a ball 9, which can be connected to a movable part of the handlebar in order to move drawbar 8 in the longitudinal direction by actuating the movable part. Drawbar 8 can transfer both tensile and shear forces in the longitudinal direction of shaft 10. Drawbar 8 is connected to scissor blades 6, 6' by an articulated joint and also forms part of working insert 30. By displacing drawbar 8 in the distal direction, scissor blades 6, 6' can be opened and closed by shifting in the proximal direction; a reverse mode of action of drawbar 8 is also conceivable, scissor blades 6, 6' being closed by displacing drawbar 8 in the distal direction and being opened by displacing it in the proximal direction. Shaft 10 is designed as a metallic shaft tube, which can be surrounded by an electrically insulating sheath 38. Electrical connections for RF voltage can be arranged on the handlebar, for example.

Figure 2:
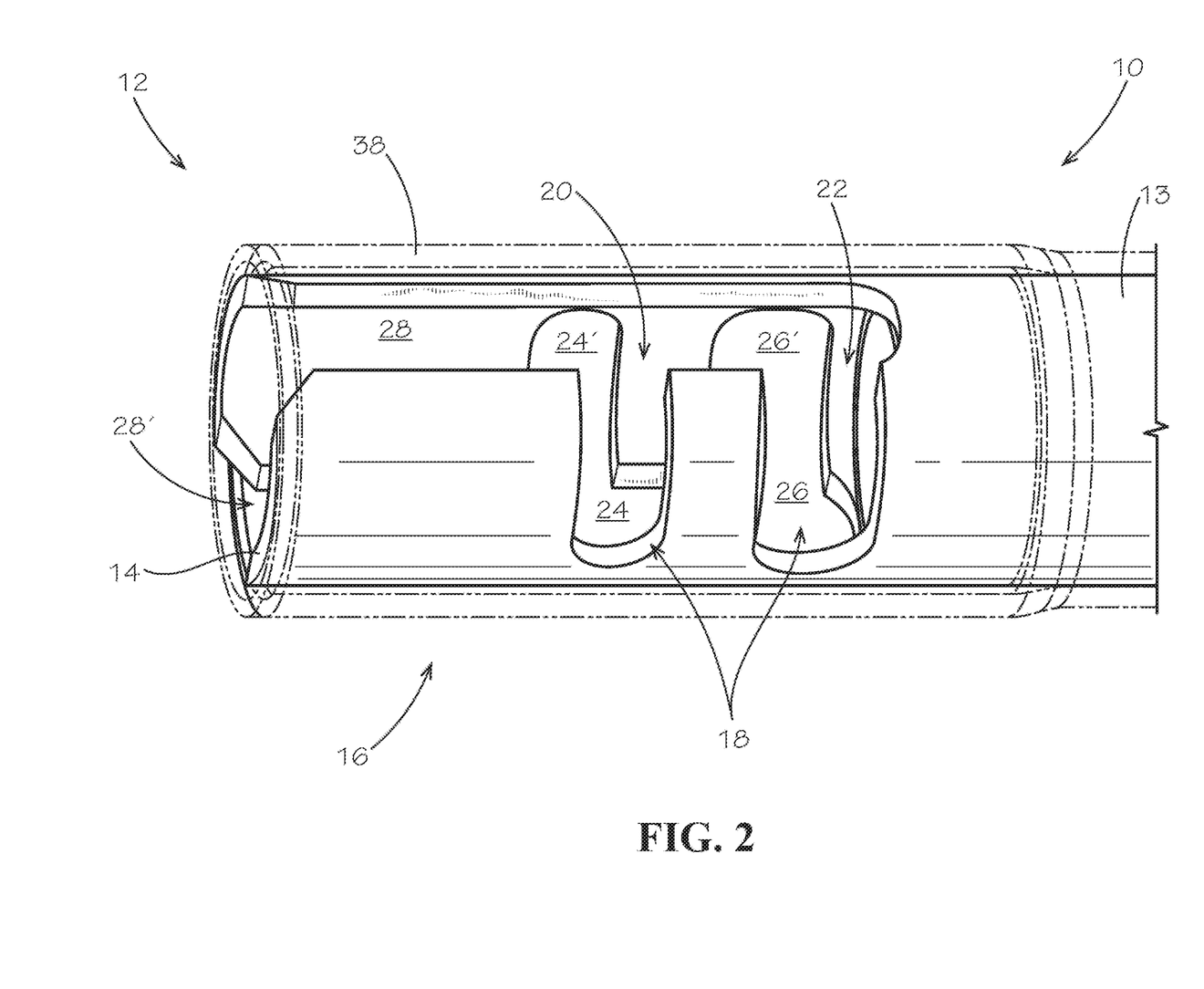
FIG. 2 shows a perspective view of the distal end section of the shaft of FIG. 1.

FIG. 2 shows a perspective view of distal end section 12 of shaft 10, which is formed by a metallic shaft tube 13. Distal end 14 of shaft 20 is formed on distal end section 12. Distal end section 12 of shaft 10 forms a connecting section 16. Connecting section 16 has a connecting device 18 for connecting a replaceable working insert, which is not shown in FIG. 2, to connecting section 16. For this purpose, connecting device 18 has a plurality of engagement structures 20, 22 for the connection engagement of different types of working inserts. To this end, a type of working insert, such as a working insert of a first type, can be brought into connection engagement with a first engagement structure 20, and by replacing the working insert with another type of working insert, such as a working insert of a second type, a connection engagement with a second engagement structure 22 can be produced, which is explained in more detail below with reference to FIGS. 3 to 6.

Engagement structures 20, 22 are designed as transverse slots 24, 26. Transverse slots 24, 26 run from a longitudinal slot 28 in a circumferential direction of shaft 10. As seen from distal end 14, transverse slots 24, 26 run clockwise from the longitudinal slot 28. Longitudinal slot 28 opens at distal end 14 of shaft 10. Longitudinal slot 24 runs along a longitudinal direction of shaft 10 or parallel to a longitudinal axis of connecting section 16. Such a connecting device 18 consisting of a longitudinal slot 28 and transverse slots 24, 26 is suitable for establishing a connection in the manner of a bayonet lock.

FIG. 2 also shows that an arrangement of a longitudinal slot 28' and two transverse slots 24', 26' is also provided in a position offset by 180° in the circumferential direction. Accordingly, connecting device 18 can advantageously have two longitudinal slots 28, 28' arranged opposite one another with respect to the longitudinal axis of connecting section 16, from which two transverse slots 24, 26 or 24', 26' start out.

Transverse slots 24, 26 are arranged at a different distance from distal end 14 and have different widths. Due to the different widths and the different distances from distal end 14, transverse slots 24, 26 form a mechanical coding. Such a mechanical coding can block the connection engagement between a type of working insert, which corresponds to the second type of working insert, and first transverse slot 24 and allow the connection engagement between this type of working insert and second transverse slot 26. In case of another type of working insert, which corresponds to the first type, a connection engagement can be established with first transverse slot 24, whereas a connection engagement can be blocked between such a type of working insert and second transverse slot 26, which will be also explained in more detail with reference to FIGS. 3 to 6. The same applies to transverse slots 24', 26' arranged opposite one another.

Figure 3:
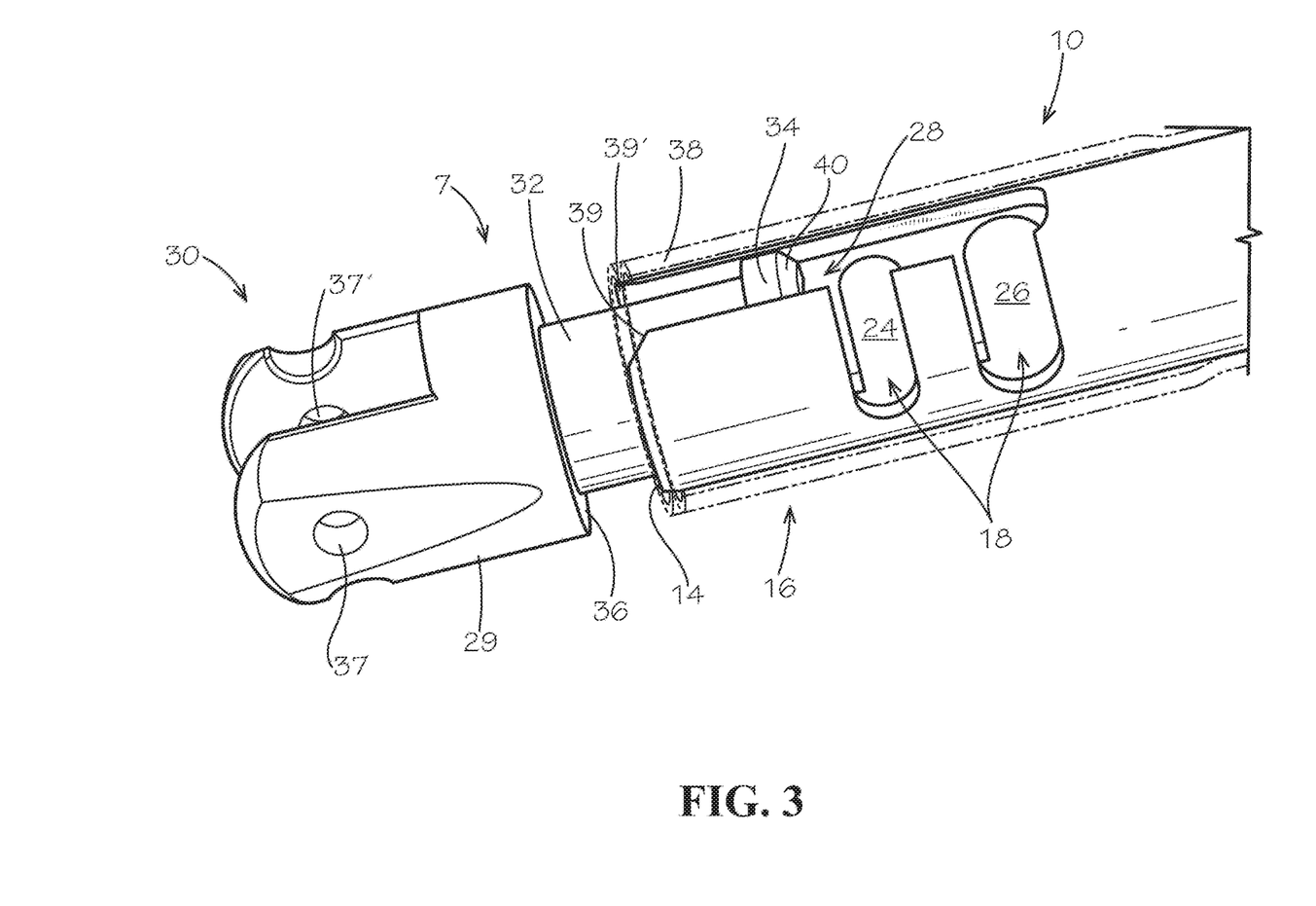
FIG. 3 shows a perspective view of the shaft of FIG. 2 with a partially inserted working insert of a first type.
Figure 4:
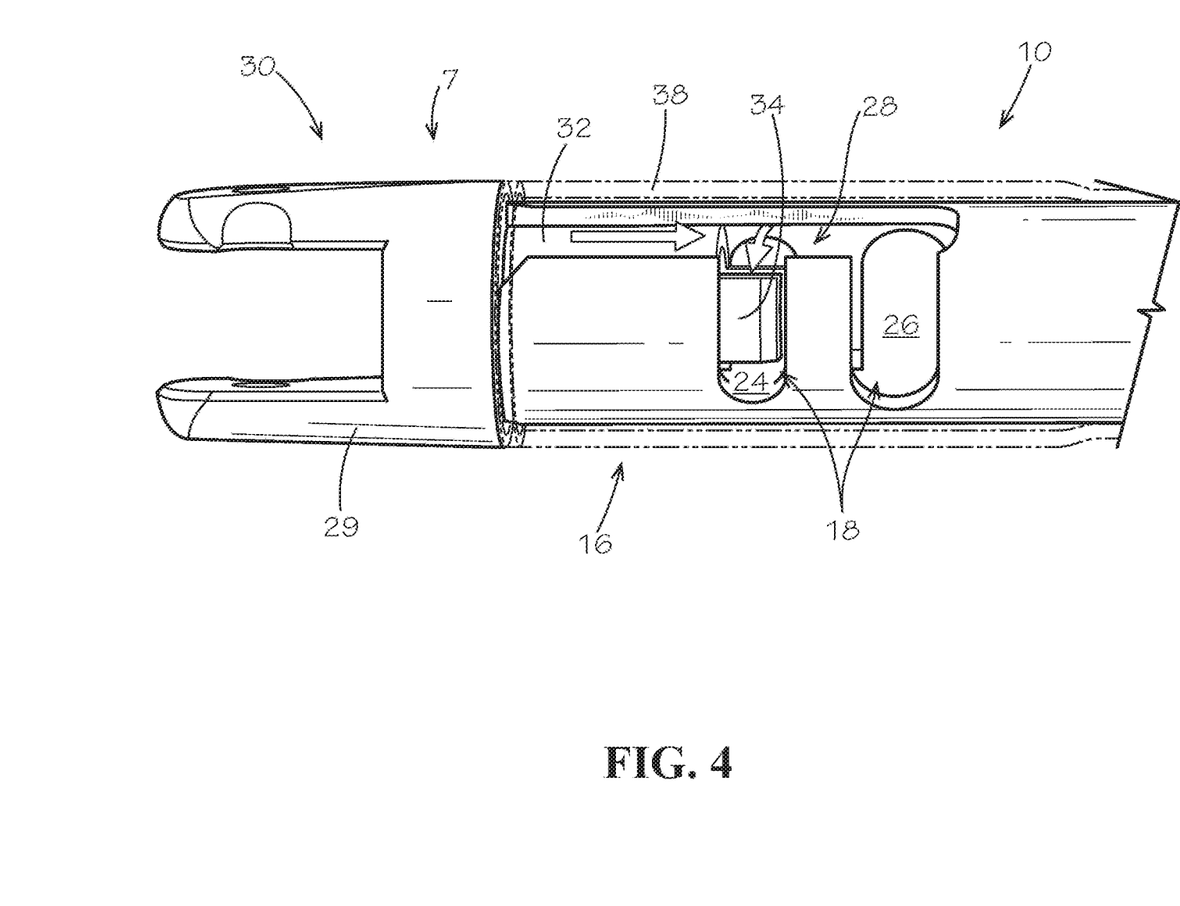
FIG. 4 shows a perspective view of the shaft of FIG. 2 with the fully inserted and connected working insert of the first type.

FIG. 3 shows a perspective view of shaft 10 with a partially inserted working insert 30 according to the first type, and in FIG. 4 working insert 30 is fully inserted into shaft 10 and connected to it.

Working insert 30 has a base 7 which comprises a fork 29 and an approximately cylindrical insertion section 32. Fork 29 is designed for the pivotable mounting of jaw parts, not shown here, of tool 5, for example scissor blades 6, 6'(see FIG. 1), and has two pivot bearings 37, 37' for this purpose. Insertion section 32 of working insert 30 can be inserted into connecting section 16 of shaft 10. A projection 34 or a plurality of projections 34 is formed at insertion section 32. Projection 34 is routed along longitudinal slot 28 when the insertion section 32 is inserted into connecting section 16 of shaft 10. In the example illustrated, two mutually oppositely arranged projections are provided, of which only one projection 34 is visible in FIG. 3. Projection 34 is routed in longitudinal slot 28, and the second projection in longitudinal slot 28'(see FIG. 2).

After insertion of insertion section 32 into connecting section 16 of shaft 10 and suitable routing of projection 34 in longitudinal slot 28, projection 34 can reach first transverse slot 24. In this position, working insert 30 can be rotated about the longitudinal axis of shaft 10, so that projection 34 comes into connection engagement with first transverse slot 24. At the same time, the second projection, which is routed through opposite longitudinal slot 28', comes into connection engagement with opposite transverse slot 24'. As a result, working insert 30 can be fixed in the longitudinal direction relative to shaft 10, as shown in FIG. 4, the axial and the subsequent circumferential movement of projection 34 being represented by arrows in FIG. 4. The connection engagement between projection 34 and transverse slot 24 can be maintained with a securing device, not shown here, or can only be released by overcoming a predetermined force, for example drawbar 8, which passes through base 7 and is connected to the jaw parts of tool 5 (see FIG. 1), can form a rotation lock.

Due to the limited length of insertion section 32 and the formation of a collar-shaped stop 36 at which insertion section 32 ends, projection 34 of working insert 30 can only be brought into engagement with transverse slot 24. Any further insertion of insertion section 32 is blocked by contacting distal end 14 by stop 36, so that projection 34 of working insert 30 of the first type of working insert cannot be brought in connection engagement with second transverse slot 26 which is further spaced apart from distal end 14.

Transverse slot 24 with the smaller width can be provided for the connection engagement with an already existing type of working insert or several types of existing working inserts, which, for example, differ with regard to the type of jaw parts, but in which insertion section 32 is designed as described above. Accordingly, first transverse slot 24 can be designed for the connection with relatively large tolerance fields 24. In connection engagement with projection 34 of working insert 30, therefore, there can be a relatively large play. However, this ensures the backward compatibility of shaft 10 with existing working inserts.

Figure 5:
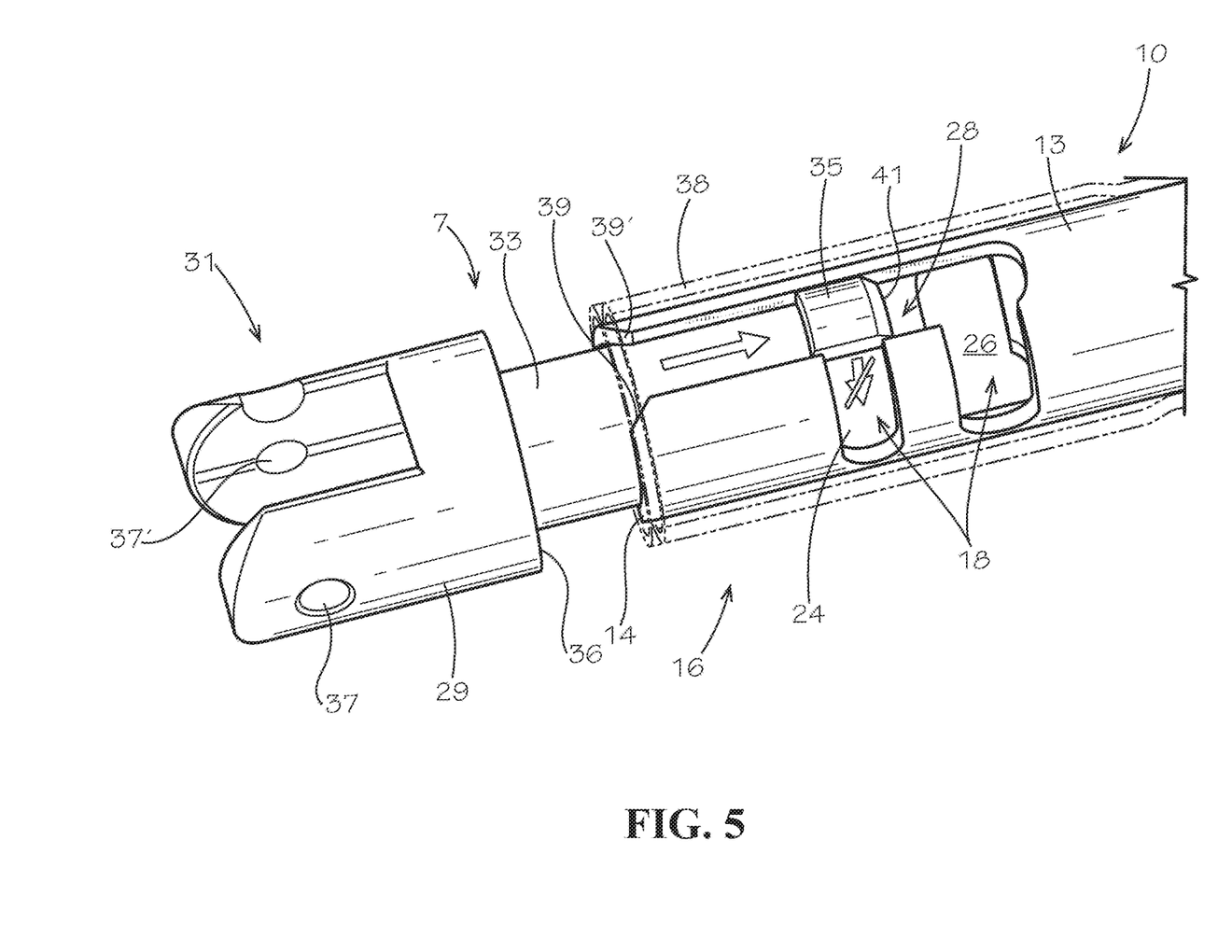
FIG. 5 shows a perspective view of the shaft of FIG. 2 with the partially inserted working insert of a second type.
Figure 6:
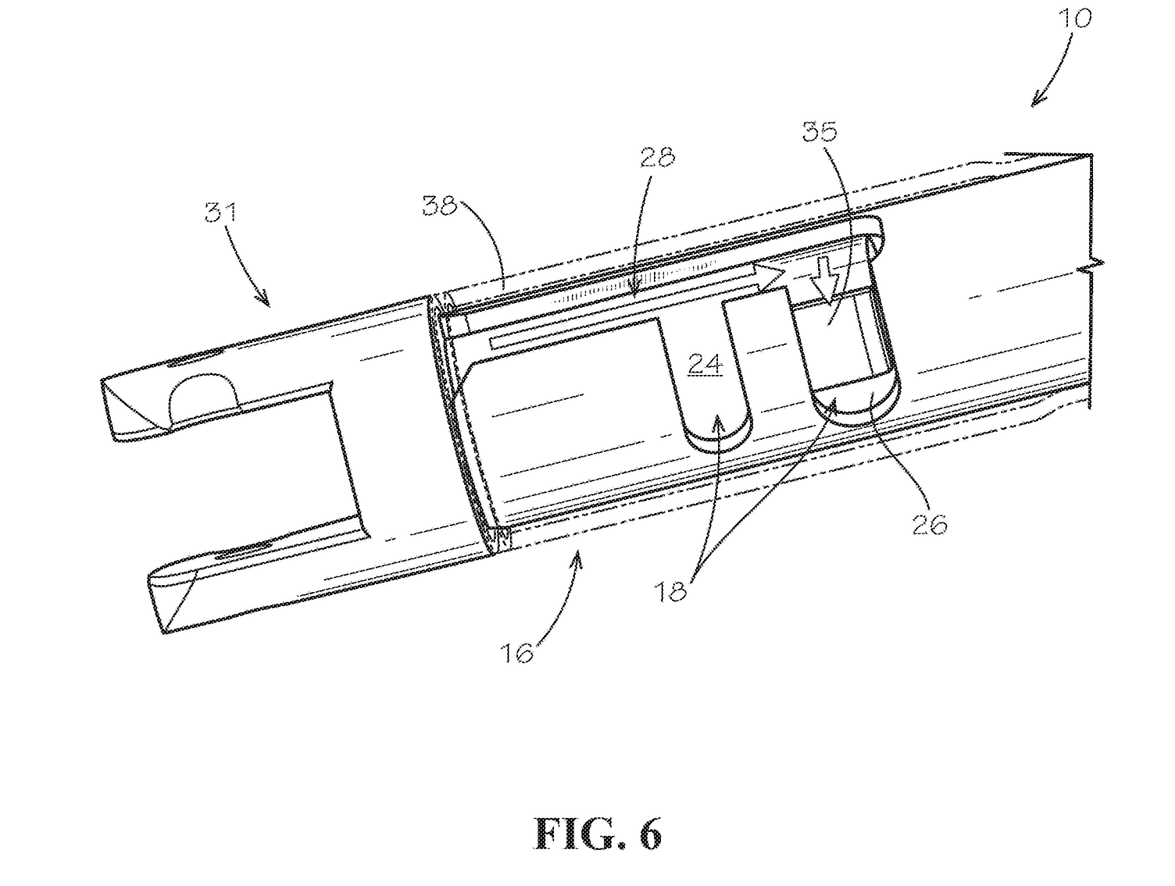
FIG. 6 is a perspective view of the shaft of FIG. 5 with the fully inserted and connected working insert of the second type.

FIG. 5 shows a perspective view of shaft 10 with a partially inserted working insert 31 of a second type, and in FIG. 6 working insert 31 is fully inserted into shaft 10 and connected to it.

Working insert 31 is a working insert of a second type, which is designed differently from previously described working insert 30. Working insert 31 also has a base 7, which comprises a fork 29 and an approximately cylindrical insertion section 33. Fork 29 is also designed for the pivotable mounting of jaw parts, not shown here, of tool 5, for example scissor blades 6, 6' or also of another type of tool such as a gripping forceps. Insertion section 33 of working insert 30 can be inserted into connecting section 16 of shaft 10. A projection 35 is formed on insertion section 33 and is routed along longitudinal slot 28 when insertion section 33 is inserted into connecting section 16 of shaft 10. In the example shown, there are also two projections 35 arranged opposite one another, of which only one projection 35 can be seen in FIG. 5.

Insertion section 33 of working insert 31 has a greater length than insertion section 32 of previously described working insert 30 of the first type. Projection 35 is thus arranged at a greater axial distance from stop 36 than in the first type of working insert described above. Working insert 31 of the second type of working insert differs from working insert 30 of the first type shown in FIGS. 2 and 3 also with regard to the dimensioning of projection 35 or the projections 35 in the longitudinal direction, wherein projection 35 or projections 35 is or are dimensioned to be larger in the axial direction than projection 34 or projections 34 of the first type of working insert. Projection 35 also will be routed along respective longitudinal slot 28 upon insertion of insertion section 33 in connecting section 16 of shaft 10. In particular, one projection 35 can be routed in a longitudinal slot 28, 28' (see FIG. 2).

After insertion of insertion section 33 into connecting section 16 of shaft 10 and suitable routing of projection 35 in longitudinal slot 28, projection 35 can reach transverse slot 24. However, due to the larger dimension of projection 35 in the longitudinal direction, it cannot be moved into transverse slot 24, which is too narrow for this purpose. The establishment of a connection engagement between projection 35 and transverse slot 24 is thus blocked. The movement of projection 35 in the axial direction and the blocked movement in the circumferential direction are indicated in FIG. 5 by the long arrow and the crossed-out arrow.

Upon further insertion of insertion section 33 into connecting section 16 of shaft 10 and a suitable routing of projection 35 in longitudinal slot 28, projection 35 can reach transverse slot 26. In this position, working insert 31 can be rotated about the longitudinal axis of shaft 10, so that projection 35 comes into connection engagement with transverse slot 26. The movement of projection 35 in the axial direction and then in the circumferential direction is indicated by the arrows in FIG. 6. As a result, working insert 31 can be fixed in the longitudinal direction relative to shaft 10. At the same time, the second projection, which is routed through opposite longitudinal slot 28', comes into connection engagement with opposite transverse slot 26'. The connection engagement between projection 34 and transverse slot 26 can be maintained with a securing device, not shown here, or can only be released by overcoming a predetermined force, for example drawbar 8, which accordingly passes through base 7 and is connected to the jaw parts of tool 5 (see FIG. 1), can form a rotation lock.

Transverse slot 26 with the greater width and at a greater distance from distal end 14 can be provided for connection engagement with new types of working insert or also with a working insert 31 which has a tool designed differently from the first type of working insert. Accordingly, transverse slot 26 can be designed for the connection with relatively narrow tolerance fields. In connection engagement with projection 35 of working insert 31, a relatively small play can therefore be implemented, so that any lost motion can be reduced or completely avoided. As mentioned above, however, transverse slot 24 arranged closer to distal end 14 ensures the backward compatibility of shaft 10 with existing types of working insert.

Simultaneously with the engagement of projection 34 or 35, stop 36 of working insert 30, 31 can abut on distal end 14 of shaft 10 or the connecting section. In this way, the handling when connecting respective working insert 30, 31 to shaft 10 can be facilitated by means of the bayonet connection. Furthermore, to simplify handling, chamfers 39, 39' can be provided on both sides of the distal mouth of longitudinal slots 28, 28' and a bevel 40, 41 can be provided on the proximal side of projections 34, 35 (see FIGS. 2 to 6). The bayonet connection is released in each case by rotating base 7 in the opposite direction about the longitudinal axis and leading insertion section 32, 33 out of connecting section 16 in the distal axial direction.

Shaft 10 can, including connecting section 16, be formed by a rigid shaft tube, for example, made of stainless steel. In the exemplary embodiment shown, shaft 10 is also equipped with a sheath 38, which consists, for example, of a plastic material and can serve for electrical insulation. In FIGS. 2 to 6, sheath 38 is shown to be transparent. In the exemplary embodiment shown, sheath 38 is slightly widened in distal end section 12 of shaft 10 to facilitate the insertion of working insert 30, 31 and the creation of the bayonet connection.

The overall result is a shaft 10 which ensures greater operational reliability or operating accuracy and, at the same time, versatility.

As has been explained above with reference to FIG. 1, shaft 10 together with working insert 30, 31 connected therein, including drawbar 8 and optionally with a handlebar attached at the proximal section 2 of shaft 10 can form a medical endoscopic instrument 1. Furthermore, shaft 10 together with multiple working inserts 30 and 31 of different types can form an endoscopic system, in particular a medical endoscopic system, or can be part of such an endoscopic system.

For the sake of clarity, not all reference numerals are shown in all figures. Reference numerals not explained for a figure have the same meaning as in the other figures.

LIST OF REFERENCE NUMERALS 1 instrument
2 proximal section
3 connection
4 connecting mechanism
5 tool
6, 6' scissor blade
7 base
8 drawbar
9 ball
10 shaft
11 middle section
12 distal end section
13 shaft tube
14 distal end
16 connecting section
18 connecting device
20 engagement structure
22 engagement structure
24, 24' transverse slot
26, 26' transverse slot
28, 28' longitudinal slot
29 fork
30 working insert
31 working insert
32 insertion section
33 insertion section
34 projection
35 projection
36 stop
37, 37' pivot bearing
38 sheath
39, 39' chamfer
40 bevel
41 bevel It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

We claim:

1. A shaft for an endoscopic instrument, with a connecting section arranged in a distal end region of the shaft, with a bayonet connecting device for connection with a replaceable working insert being formed at the connecting section, the bayonet connecting device having a first engagement structure for a connection engagement with a first type working insert, characterized in that the bayonet connecting device has a second engagement structure for a connection engagement with a second type working insert, wherein the first and the second engagement structures are arranged and/or formed differently; and     wherein the first engagement structure permits the connection engagement with a first engagement element of the first type working insert and blocks a connection engagement with a second engagement element of the second type working insert and the second engagement structure permits the connection engagement with the second engagement element of the second type working insert and blocks a connection engagement with the first engagement element of the first type working insert;

characterized in that the second engagement element is longer than the first engagement element;

characterized in that at least one first engagement structure and at least one second engagement structure are each formed by a transverse slot or a transverse groove, the transverse slots or transverse grooves being formed for the longitudinal fixing of the engagement element of a working insert according to the first or the second type; and characterized in that one of the transverse slots or the transverse grooves of at least one first engagement structure and at least one second engagement structure is at a greater distance from the distal end of the connecting section and has a greater width than one of the transverse slots or the transverse grooves of at least one first engagement structure and at least one second engagement structure at a smaller distance from the distal end.

\* \* \* \* \*